United States Patent [19]
Gold et al.

[11] Patent Number: 6,125,843
[45] Date of Patent: Oct. 3, 2000

[54] LIQUID SPRAY DISPENSER AND METHOD

[75] Inventors: Scott Gold, New York; John V. Mizzi, Poughkeepsie, both of N.Y.

[73] Assignee: Pincgold LLC, New York, N.Y.

[21] Appl. No.: 08/923,152

[22] Filed: Sep. 4, 1997

[51] Int. Cl.[7] .................................................. A61M 11/00
[52] U.S. Cl. ............................... 128/200.23; 128/203.23
[58] Field of Search ......................... 128/200.23, 203.23, 128/203.24, 205.24, 207.18; 601/150, 161; 137/826; 239/338, 500, 502

[56] References Cited

U.S. PATENT DOCUMENTS

| | | | |
|---|---|---|---|
| 238,388 | 3/1881 | Heine | 239/588 |
| 423,198 | 3/1890 | Windolph | 128/200.14 |
| 790,318 | 5/1905 | Sams | 128/200.14 |
| 2,331,117 | 10/1943 | Goodhue et al. | 128/200.14 |
| 3,529,774 | 9/1970 | Apri | 239/581.1 |
| 4,583,531 | 4/1986 | Mattchen | 601/161 |
| 4,655,197 | 4/1987 | Atkinson | 604/30 |
| 4,930,997 | 6/1990 | Bennett | 417/410 |
| 4,934,358 | 6/1990 | Nilsson et al. | 128/200.23 |
| 5,020,526 | 6/1991 | Epstein | 128/200.14 |
| 5,046,486 | 9/1991 | Grulke et al. | 601/161 |
| 5,505,193 | 4/1996 | Ballini et al. | 128/200.14 |
| 5,819,801 | 10/1998 | Palffy | 137/826 |
| 5,921,233 | 7/1999 | Gold et al. | 128/200.22 |

OTHER PUBLICATIONS

*Suction Devices;* Thom Dick, *JEMS;* Mar. 1985, pp. 30–46.

*Primary Examiner*—Aaron J. Lewis
*Assistant Examiner*—Teena Mitchell
*Attorney, Agent, or Firm*—R. Neil Sudol; Henry D. Coleman

[57] ABSTRACT

A liquid dispenser for medical applications includes a pressurized liquid container, a nozzle, and a conduit or flow guide connected to the container and the nozzle for defining a flow path between the container and the nozzle. A manually actuatable flow rate control mechanism is operatively coupled to the conduit or flow guide and is manipulable by a user to adjust an average rate of flow of liquid from the container to the nozzle. In addition, a manually actuatable pulse rate control mechanism is operatively coupled to the conduit or flow guide and is manipulable by a user to adjust a rate of pulsation in liquid flowing from the container to the nozzle. The invention thus enables a user to set flow rate and pulsation frequency as desired.

29 Claims, 3 Drawing Sheets

LIQUID SPRAY DISPENSER AND METHOD

BACKGROUND OF THE INVENTION

This invention relates to a liquid dispenser. More particularly, this invention relates to a liquid spray dispenser utilizable in irrigating nasal passages.

Spray dispensers for treating nasal passages are well known.

A particular use for nasal sprays is in cleaning nasal passages which have been subjected to surgery or other therapeutic procedure. The tissues at a surgical site are obviously prone to clotting and the aggregation of contaminants and possible infectious agents which may inhibit healing. A hand held nasal irrigation device for cleaning surgically treated nasal tisses would be of use to patients.

OBJECTS OF THE INVENTION

An object of the present invention is to provide a liquid dispenser device.

A more specific object of the present invention is to provide a hand-held liquid spray device.

An even more specific object of the present invention is to provide such a liquid spray device which is useful for spraying or irrigating nasal passages, for example, nasal passages which have been subjected to surgery and require periodic cleaning during a convalesent period.

Another object of the present invention is to provide such a liquid dispenser device or liquid spray device which may be manually adjusted to vary selected dispensing parameters.

It is also an object of the present invention to provide a liquid dispenser device or liquid spray device which is utilizable to irrigate nasal passages with a fluid in either a steady flow or a pulsatile flow.

It is another object of the present invention to provide a liquid dispenser device or liquid spray device which is utilizable with commercially available aerosol containers having existing product fillings, propellants and standard valves.

Yet another object of the present invention is to provide a method for irrigating nasal passages.

These and other objects of the present invention will be apparent from the descriptions and drawings herein.

SUMMARY OF THE INVENTION

A liquid dispenser for medical applications comprises, according to the present invention, a pressurized liquid container, a nozzle, and a conduit or flow guide connected to the container and the nozzle for defining a flow path between the container and the nozzle. A manually actuatable flow rate control mechanism is operatively coupled to the conduit or flow guide and is manipulable by a user to adjust an average rate of flow of liquid from the container to the nozzle. In addition, a manually actuatable pulse rate control mechanism is operatively coupled to the conduit or flow guide and is manipulable by a user to adjust a rate of pulsation in liquid flowing from the container to the nozzle. The invention thus enables a user to set flow rate and pulsation frequency as desired.

According to a feature of the invention, the flow rate control mechanism and the pulse rate control mechanism are disposed in a housing removably connected to the container. In that case, the nozzle is advantageously disposed at a free end of a resiliently bendable tube removably connected at an opposite end to the housing. The bendable tube facilitates the positioning of the nozzle at the entrance of a nostril, whereas the separability of the nozzle tube from the housing enables the use of the same housing by different family members, who preferably have their own nozzle tubes. The nozzle tubes are preferably provided with respective one-way nozzles to prevent flow of an irrigant from the tubes back to the housing.

The separability of the housing from the liquid container also enables the use of the control portion of the dispenser device with different liquid containers. Where the container is provided with a spring-loaded valve port, the housing is shiftably mounted to the container at the valve port for opening the valve port and thereby enabling flow of liquid from the container into the housing via the valve port upon a shifting of the housing towards the container.

Generally, it is contemplated that the liquid is a sterile saline solution, including, for instance, sodium bicarbonate. However, other liquids, adapted for specific therapeutic purposes, may be provided.

Pursuant to a specific embodiment of the present invention, the pulse rate control mechanism includes a spring loaded valve. The spring loaded valve is shiftable under fluid pressure from a bellows element. In an alternative embodiment of the invention, the pulse rate control mechanism includes a peristaltic motor driven by fluid pressure from the container.

Preferably, the nozzle has an adjustable spray pattern. For example, the nozzle may be rotatable about an axis of the nozzle tube so as to have a first angular position for ejecting liquid in a mist or spray pattern and a second angular position for ejecting liquid in a stream pattern.

The flow rate control mechanism preferably includes a pinch valve.

A method for dispensing a liquid comprises, in accordance with the present invention, manually adjusting a flow rate control mechanism disposed at an outlet of a hand-held container holding a pressurized liquid to be dispensed. Adjusting the flow rate control mechanism serves to control an average rate of flow of liquid from the container to a nozzle. The method also comprises manually adjusting a pulse rate control mechanism disposed at an outlet of the container, to thereby control a rate of pulsation in liquid flowing from the container to the nozzle, and manually opening a valve to enable liquid flow from the container to the nozzle via the flow rate control mechanism and the pulse rate control mechanism.

Where the flow rate control mechanism and the pulse rate control mechanism are disposed in a housing, the method further comprising removably connecting the housing to the container. Where the nozzle is disposed at a free end of a resiliently bendable tube, the method also comprises removably connecting the tube at an end opposite the nozzle to the housing. Wherein the container has an outlet port provided with the valve, the manual opening of the valve includes shifting the housing towards the container.

As discussed above with reference to the apparatus of the invention, the pulse rate control mechanism may include a spring loaded valve having a spring. In that case, the method further comprises periodically stressing the spring during a flow of liquid from the container to the nozzle. For example, the spring is repeatedly compressed and released, with a periodicity corresponding to the pulsation frequency of the irrigant. The manual adjusting of the pulse rate control mechanism includes modifying a rest-state load on the spring. For example, increasing the degree of compression of the spring when no irrigant is flowing reduces the pulsation frequency, while decreasing the degree of spring compression increases the frequency.

If the pulse rate control mechanism includes a peristaltic motor, the method includes driving the motor by fluid pressure from the container during a flow of liquid from the container to the nozzle. The manual adjusting of the pulse rate control mechanism includes shifting an impediment to liquid flow in the motor.

As described above, the flow rate control mechanism may include a pinch valve disposed in operative contact with a flexible tubular flow guide. Then adjusting of the flow rate control mechanism includes modifying a state of compression of the flow guide.

A liquid spray device in accordance with the present invention is useful for spraying or irrigating nasal passages, for example, nasal passages which have been subjected to surgery and require periodic cleaning during a convalescent period. The liquid dispenser device or liquid spray device is manually adjustable to vary flow rate and pulsation frequency. Thus, the device is adaptable by the individual user as desired.

A liquid dispenser device or liquid spray device in accordance with the present invention is utilizable with commercially available aerosol containers having existing product fillings, propellants and standard valves.

DESCRIPTION OF THE PREFERRED EMBODIMENTS

Figure 1:
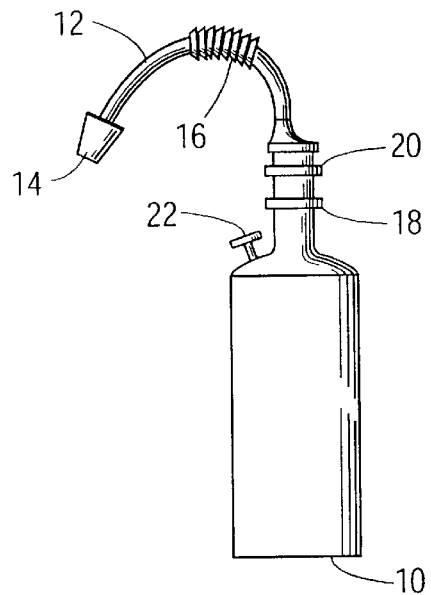
FIG. 1 is a schematic side elevational view of a liquid dispensing device particularly utilizable as a nasal irrigator in accordance with the present invention.

As shown in FIG. 1, a nasal irrigator comprises a cylindrical container 10 which has an elongate irrigation tube 12 for delivering fluid under pressure to a person's nasal passage. Tube 12 has a free end provided with a nozzle 14 which may be adjusted for changing the shape of the dispensed liquid from a jet to a spray and vice versa. Tube 12 is corrugated at 16 in the manner of a drinking straw to enable adjustment of an angle of nozzle 14 relative to an axis (not shown) of container 10 and thereby facilitate use of the nasal irrigator.

At a top of container 10, and at a base or inlet end of tube 12, are provided two rotary controls 18 and 20 for varying other parameters of liquid application. One rotary control 18 changes the average volume flow rate while the other control 20 modifies the variation about that average--from an even flow to a pulsatile flow and vice versa.

As further shown in FIG. 1, a push button 22 is provided for alternately turning the flow of irrigant on and off Normally, container 10 is closed and no irrigant travels along tube 12. Pushing button 22 opens a valve 24 (FIG. 2) and allows irrigant to flow under pressure from the container 10. Container 10 is pressurized in a conventional manner, for example, by mixing liquid components to produce a gas.

Figure 2:
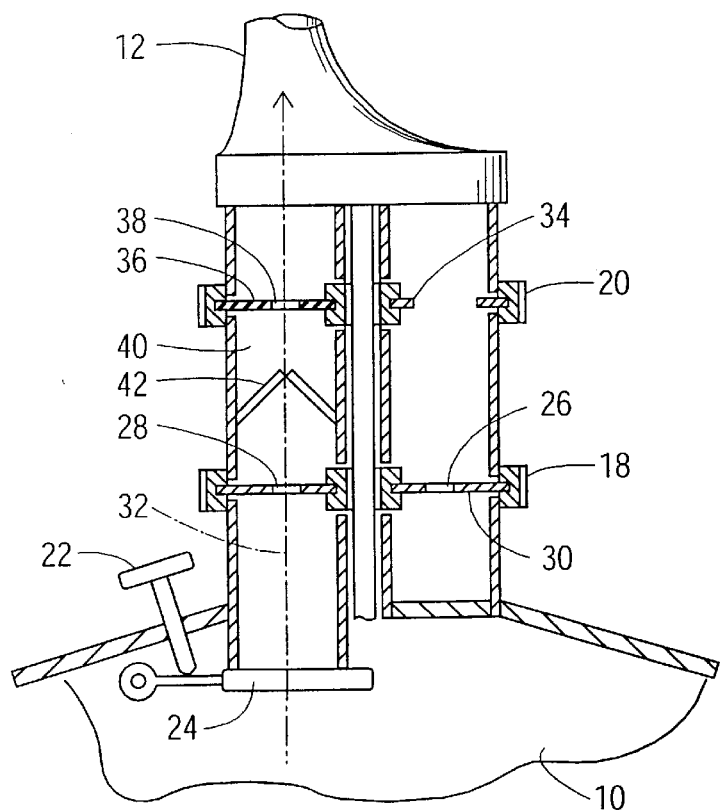
FIG. 2 is a schematic partial cross-sectional view of the device of FIG. 1, taken parallel to the plane of FIG. 1.

FIG. 2 illustrates specific valve structures actuated by rotating controls 18 and 20. Control knob 18 is connected to a disk 26 provided with a plurality of apertures 28 and 30 of different diameters. Rotating this control knob 18 places different apertures into a flow path 32 extending from valve 24 to tube 12.

Control knob 20 is connected to another disk 34 which carries at least one flexible membrane 36. Membrane 36 is provided with a slit 38 which is substantially closed at low pressures. FIG. 2 shows disk 34 positioned so that membrane 36 is disposed in flow path 32. Upon the filling of a chamber 40 on an upstream side of membrane 36 with fluid above a threshold pressure, membrane 36 deforms, thereby opening slit 38 ad permitting the fluid contained in chamber 40 to exit towards tube 12. A one-way valve 42 may be provided on an upstream side of disk 34 in flow path 32 for defining chamber 40 and assisting in a periodic emptying of chamber 40.

Figure 3:
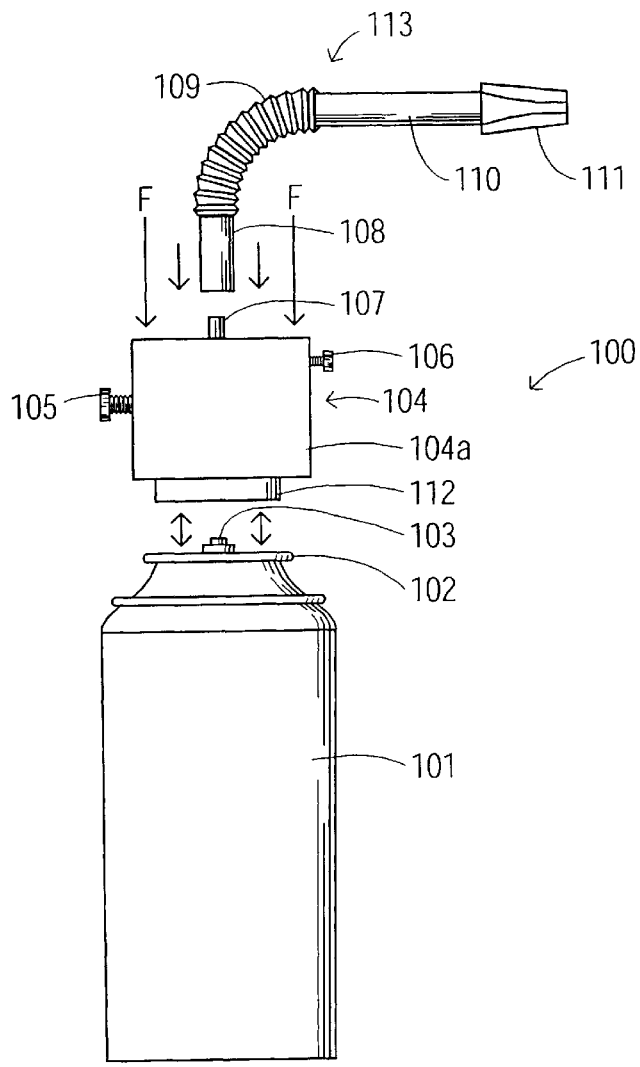
FIG. 3 is a schematic side elevational view, in an exploded format, of another liquid dispensing device or nasal irrigator in accordance with the present invention.

As depicted in FIG. 3, another nasal irrigator 100 comprises three functional modules 101, namely, a dispenser or irrigant container 101, a pulsator module 104 and a nasal tube 113, which removably couple to one another. Container 101 is provided with a standard aerosol valve 103 crimped to a rolled container collar 102. Preferably, container 101 takes the form of a barrier pack using compressed air as the propellant. Compressed air is environmentally benign and cannot increase in pressure to a level which could damage nasal passages when stored at elevated temperatures (as in the case of hydrocarbons and some other liquid propellants). An example of commercially available containers of this type is the EP Spray System of Neuchatel, Switzerland. That system uses a multilayer pouch which separates the product from the air propellant.

Generally, the dispensed liquid product of a nasal irrigator can be a sterile saline solution, including, for instance, sodium bicarbonate. Of course, various additives may be included in the irrigant, such as antibacterial components and fragrances.

Pulsator module 104 snaps onto container valve collar 103. This releasable snap-lock fit is implemented by a collar 112 on pulsator module 104. Collar 112 fits within rolled container collar 102 for mechanical guidance.

Pulsator module 104 includes a housing 104a on which is provided a screw control 105 for enabling a user to adjust a rate of pulsation of irrigant from zero (no pulsation) to a maximum rate on the order of 1000 pulses per minute. Pulsator module 104 is provided with a second screw control 106 for adjusting an average flow rate. Flow is started and stopped via valve 103: exerting a force F on pulsator housing 104a towards container 101 causes irrigant to begin flowing. Controls 105 and 106 are partially interactive insofar as flow rate affects pulsation rate. Both controls 105 and 106 can be eliminated, if desired, by selecting a setting at the factory. Such a dispensing device or nasal irrigator having a preset flow rate and a preset pulsation rate would be less expensive to produce and would have enhanced reliability.

Pulsator housing 104a is provided on one side with a coupling nipple 107 which is inserted, in a friction fit, into a tubular connector portion 108 of nasal tube 113. Connector portion 108 is connected to a corrugated section 109 of tube 113 which is in turn connected to a fluted discharge nozzle 111 via a semi-rigid straight section 110. Corrugated section 109 enables a user to vary an angle of straight tube section 110 with respect to connector portion 108 and hence with respect to coupling nipple 107. Nozzle 111 is preferably adjustable for enabling a user to changing the dispensed liquid from a jet to a spray and vice versa.

Figure 4:
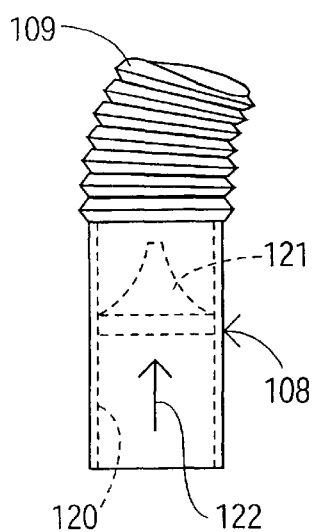
FIG. 4 is a schematic side elevational view of a detail of the device of FIG. 3.

As illustrated in FIG. 4, connector portion 108 is provided with a check valve 121 which permits flow in a discharge direction 122 only. Check valve 121 prevents reflux of any contaminated nasal irrigant back into pulsator module 104. For this purpose, a positive closing check valve 121 such as a "duck bill" type is required.

An inner cylindrical surface 120 of connector potion 108 engages an outer surface (not designated) of coupling nipple 107 in a releasable friction fit. Thus, several individuals may use a single container 101 and a single pulsator module 104. Each individual has his or her own nasal tube 113 and removably attaches that tube to coupling nipple 107 prior to use of the nasal irrigator device. Container 101 is factory filled and pressurized. Pulsator module 104 is cleaned and transferred to a new container 101 when the prior container is depleted of nasal irrigant product. Tubes 113 may be manufactured in different colors to facilitate identification by the respective users.

Figure 5:
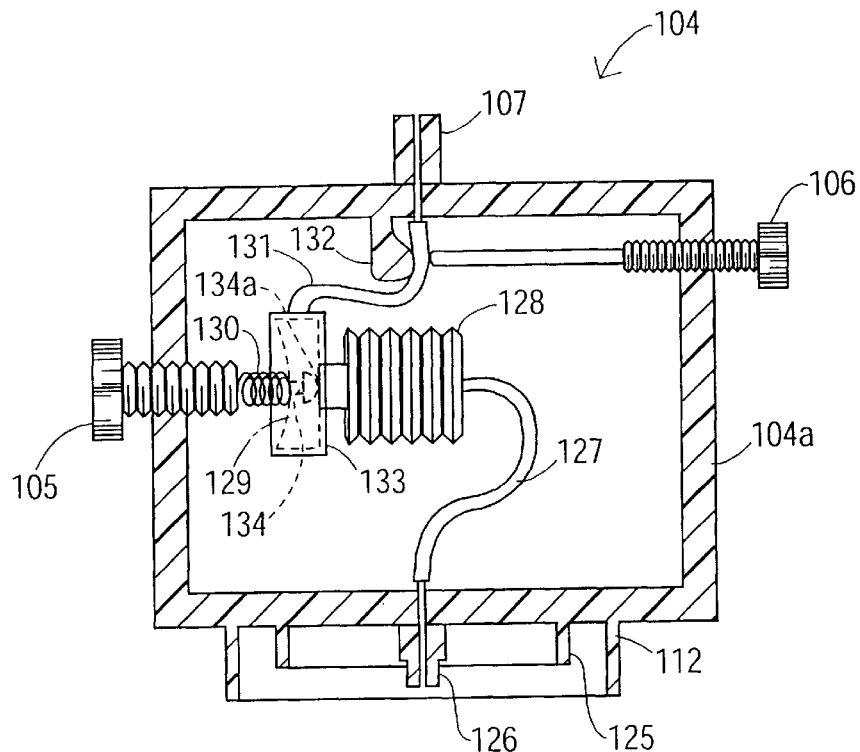
FIG. 5 is a schematic cross-sectional view of a component of the device of FIG. 3, taken parallel to the plane of FIG. 3.

As shown in FIG. 5, pulsator module housing 104 is provided along a lower side with a nipple 126 which is received in aerosol valve 103 (FIG. 3) of container 101. The lower side of housing 104a is further provided with a circular ring or flange 125 which is also part of the mechanism for coupling pulsator module 104 to container 101. Nipple 126 is coupled via a flexible conduit 127 to an inlet side of a storage bellows 128.

Upon an application of force F (FIG. 3) to pulsator module 104, fluid is conveyed under pressure from container 101 through valve 103, nipple 126 and conduit 127 to bellows 128. Bellows 128 is molded so as to be biased toward a longitudinally collapsed configuration and to be longitudinally expanded by fluid pressure. At an end opposite conduit 127, bellows 128 is provided with a valve seat 134a which is essentially coplanar with a wall (not labeled) of a chamber or compartment 133. A conical valve 134 disposed in chamber 133 coacts with valve seat 134a to block flow of irrigant fluid into chamber 133 until the differential pressure across valve 134 is high enough to push valve 134 off of valve seat 134a. At that juncture, fluid enters chamber 133 from bellows 128 and causes a diaphragm 129 to snap from a stable inwardly convex position (shown in the drawing) to a stable outwardly convex position. Bellows 128 partially empties, even though fluid continues to enter the bellows via conduit 127.

Diaphragm 129 has a hysteresis type behavior in that the pressure within chamber 133 must fall a significant amount before a spring 130 urges diaphragm 129 past its metastable position to snap back into the inwardly convex position shown in FIG. 5. At that point in an operating cycle of pulsator module 104, valve 134 again engages seat 134a and blocks flow through pulsator module 104 to nasal tube 113. Bellows 128 continues to elongate and to build pressure within until the entire cycle repeats.

Screw 105 is used to vary a compression level of spring 130 and concomitantly an additional biasing force on diaphragm 129. A lower compression level will cause valve 134 to unseat at a lower pressure and with bellows 128 at a smaller capacity. Consequently, owing to a reduction in the time required to fill bellows 128 to this lower pressure, the rate of pulsations applied to the fluid flow through pulsator module 104 would increase. Further relief in the compression of spring 130 will eventually unseat valve 134 permanently, thereby enabling a steady irrigant flow through pulsator module 104. Increasing the compression of spring 130 will raise the threshold pressure necessary to unseat valve 134, causing longer time delays and concomitant filling of bellows 128 to larger volumes. Increasing the compression of spring 130 thus results in a slower rate of pulsation in irrigant flow.

As further shown in FIG. 5, screw 106 is an actuator of a simple pinch valve wherein a flexible conduit 131 extending from chamber 133 to nipple 107 is pinched against a wall protrusion 132.

Figure 6:
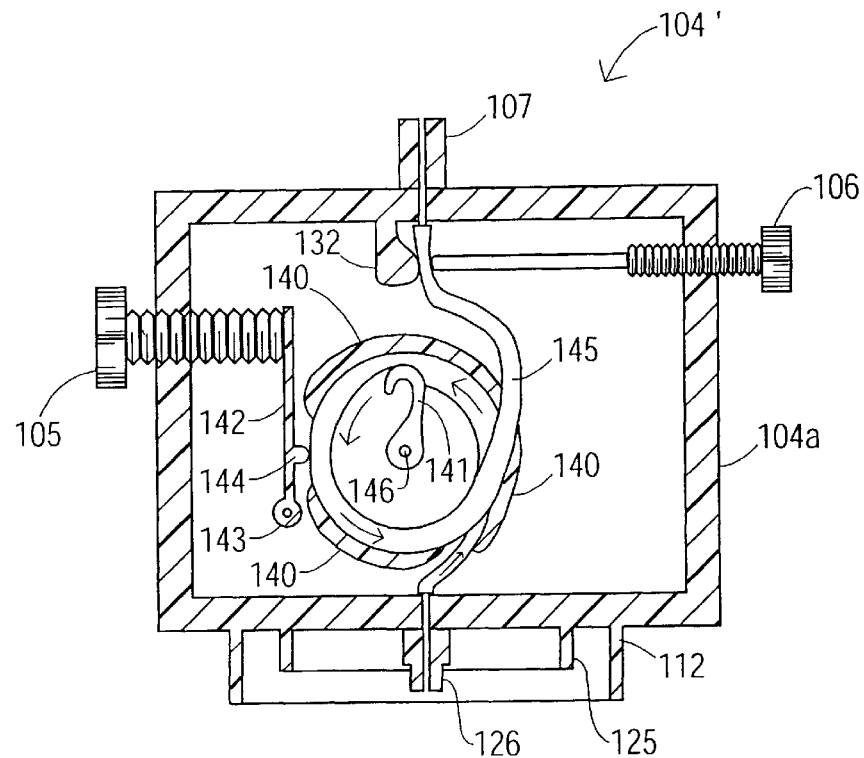
FIG. 6 is a schematic cross-sectional view similar to FIG. 5 showing an alterative design to the component of FIG. 5.

FIG. 6 illustrates an alternate pulsator module 104' wherein similar elements are designated with the same reference numerals as in FIG. 5. The pulsator mechanism of FIG. 6 is a peristaltic motor driven by the fluid pressure of the irrigant. A very flexible conduit 145 extends from nipple 126 on an inlet side to nipple 107 on an outlet side. Conduit 145 is made of silicone tubing or another similarly resilient material and has a central segment maintained in a circular loop configuration by a plurality of circular wall elements 140 fastened to a wall (not labeled) of pulsator housing 104a. A rotor arm 141 rotatably attached to housing 104a via a pivot pin 146 is urged in a forward (counterclockwise) direction by a slight bulge in conduit 145. To enable a variation in a pulsation rate of irrigant flow, an adjustment arm 142 is pivotably mounted to housing 104a (as depicted in FIG. 5) via a pin 143 and is provided with a boss 144 which 20 engages conduit 145. Arm 146 is engageable at a free end by pulse rate adjusting screw 105. If arm 142 were omitted, rotor 141 would rotate continuously and irrigant flow would be essentially continuous. However, with boss 144 pressed against conduit 145 to a degree determined by the turning of screw 105, a heightened friction encountered by rotor 141 in the vicinity of the boss causes the rotor to stop, thereby occluding irrigant flow. As pressure builds behind the stopped rotor 141, an "aneurism" or bulge in conduit 145 behind rotor 141 enlarges and pushes harder against rotor 141 until the rotor is dislodged and flow resumes. Unscrewing screw 105 outwardly increases pulse rate and further adjustment in the same direction will result in a steady flow. Shifting screw 105 inwardly will reduce the pulse rate. It is to be noted that rotor 141 must have a very low-friction conduit contact region (e.g., polytetrafluoroethylene). Alternatively, rotor 141 may be fitted at its free end with a roller (not shown) engaging conduit 145.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof

What is claimed is:

1. A liquid dispenser for medical applications, comprising:
   a pressurized liquid container provided with a spring-loaded valve port;
   a housing removably mounted to said pressurized liquid container at said valve port for opening said valve port and thereby enabling flow of liquid from said pressurized liquid container into said housing via said valve port;

a nozzle operatively connected to said housing;

a flow rate control mechanism disposed in said housing to determine an average rate of flow of liquid from said container through said housing to said nozzle; and a pulse rate control mechanism disposed in said housing to determine a rate of pulsation in liquid flowing from said pressurized liquid container through said housing to said nozzle.

2. The dispenser defined in claim 1 wherein said nozzle is disposed at a free end of a resiliently bendable tube removably connected at an opposite end to said housing.

3. The dispenser defined in claim 1 wherein said housing is shiftably mounted to said container at said valve port for opening said valve port and thereby enabling flow of liquid from said container into said housing via said valve port upon a shifting of said housing towards said container.

4. The dispenser defined in claim 1 wherein said pulse rate control mechanism includes a spring loaded valve.

5. The dispenser defined in claim 4 wherein said pulse rate control mechanism further includes a bellows element.

6. The dispenser defined in claim 1 wherein said pulse rate control mechanism includes a peristaltic motor driven by fluid pressure from said pressurized liquid container.

7. The dispenser defined in claim 1 wherein said nozzle has an adjustable spray pattern.

8. The dispenser defined in claim 7 wherein said nozzle has a first position for ejecting liquid in a mist or spray pattern and a second position for ejecting liquid in a stream pattern.

9. The dispenser defined in claim 1 wherein said pressurized liquid container is a hand-held pressurized liquid container.

10. The dispenser defined in claim 1 wherein said flow rate control mechanism includes a pinch valve.

11. The dispenser defined in claim 1 wherein said housing is shiftably mounted to said container to alternately open and close said valve port, thereby providing a user-actuatable valve operatively connected to said container for enabling the user to alternately open and block liquid flow from said container through said housing to said nozzle.

12. The dispenser defined in claim 1 wherein said flow rate control mechanism and said pulse rate control mechanism are independently manually actuatable.

13. A device for use in dispensing a liquid, comprising:

a housing;

an inlet port on said housing connectable to a pressurized liquid-holding container;

an outlet port on said housing;

a flow rate control mechanism manipulable by a user and mounted to said housing for adjusting an average rate of flow of liquid from said inlet port to said outlet port after connection of said inlet port to the pressurized liquid-holding container; and a pulse rate control mechanism manipulable by a user and mounted to said housing for adjusting a rate of pulsation in liquid flowing from said inlet port to said outlet port, said pressurized liquid-holding container being provided with a spring-loaded valve port, said housing being shiftably mountable to said container at said valve port for opening said valve port and thereby enabling flow of liquid from said container into said housing via said valve port and said inlet port upon a shifting of said housing towards said container.

14. The device defined in claim 13, further comprising a nozzle disposed at a free end of a resiliently bendable tube removably connected at an opposite end to said housing at said outlet port.

15. The device defined in claim 14 wherein said nozzle has an adjustable spray pattern.

16. The device defined in claim 15 wherein said nozzle has a first position for ejecting liquid in a mist or spray pattern and a second position for ejecting liquid in a stream pattern.

17. The device defined in claim 13 wherein said pulse rate control mechanism includes a spring loaded valve.

18. The device defined in claim 17 wherein said pulse rate control mechanism further includes a bellows element.

19. The device defined in claim 13 wherein said pulse rate control mechanism includes a peristaltic motor driven by fluid pressure from said container.

20. The device defined in claim 13 wherein said flow rate control mechanism includes a pinch valve.

21. A method for dispensing a liquid, comprising:

providing a hand-held container holding a pressurized liquid to be dispensed, said container having an outlet port provided with a valve;

further providing a flow rate control mechanism and a pulse rate control mechanism disposed in a housing;

removably connecting said housing to said container;

manually adjusting said flow rate control mechanism to thereby control an average rate of flow of liquid from said container to a nozzle;

manually adjusting said pulse rate control mechanism to thereby control a rate of pulsation in liquid flowing from said container to said nozzle; and manually opening a valve to enable liquid flow from said container to said nozzle via said flow rate control mechanism and said pulse rate control mechanism, the manual opening of said valve including shifting said housing towards said container.

22. The method defined in claim 21 wherein said nozzle is disposed at a free end of a resiliently bendable tube, further comprising removably connecting said tube at an end opposite said nozzle to said housing.

23. The method defined in claim 21 wherein said pulse rate control mechanism includes a spring loaded valve having a spring, further comprising periodically stressing said spring during a flow of liquid from said container to said nozzle, the manual adjusting of said pulse rate control mechanism including modifying a rest-state load on said spring.

24. The method defined in claim 21 wherein said pulse rate control mechanism includes a peristaltic motor, further comprising driving said motor by fluid pressure from said container during a flow of liquid from said container to said nozzle, the manual adjusting of said pulse rate control mechanism including shifting an impediment to liquid flow in said motor.

25. The method defined in claim 21 wherein said flow rate control mechanism includes a pinch valve disposed in operative contact with a flexible tubular flow guide, the adjusting of said flow rate control mechanism including modifying, a state of compression of said flow guide.

26. A self-contained liquid dispenser for medical applications, comprising:

a hand-holdable housing;

a pressurized liquid container removably connected to and carried on said housing so as to be hand-holdable therewith;

a nozzle mounted to said housing so as to be hand holdable therewith;

flow path means operatively connected to said housing and said nozzle for defining a flow path between said container and said nozzle;

a flow rate control mechanism operatively coupled to said flow path means and disposed in said housing to determine an average rate of flow of liquid from said container to said nozzle; and a pulse rate control mechanism operatively coupled to said flow path means and disposed in said housing to determine a rate of pulsation in liquid flowing from said container to said nozzle.

27. The dispenser defined in claim 26 wherein said pressurized liquid container is provided with a valve at an outlet port, said housing being formed with an actuator for opening said valve after connection of said housing to said container.

28. The dispenser defined in claim 27 wherein said valve is spring loaded, said housing being shiftably mounted to said pressurized liquid container at said valve for opening said valve and thereby enabling flow of liquid from said pressurized liquid container into said housing via said valve upon a shifting of said housing towards said container.

29. A method for dispensing a liquid, comprising:

providing a hand-held container holding a pressurized liquid to be dispensed;

manually adjusting a flow rate control mechanism disposed at an outlet of said container, to thereby control an average rate of flow of liquid from said hand-held container to a nozzle, said flow rate control mechanism including a pinch valve disposed in operative contact with a flexible tubular flow guide, the adjusting of said flow rate control mechanism including modifying a state of compression of said flow guide;

manually adjusting a pulse rate control mechanism disposed at an outlet of said container, to thereby control a rate of pulsation in liquid flowing from said container to said nozzle; and manually opening a valve to enable liquid flow from said container to said nozzle via said flow rate control mechanism and said pulse rate control mechanism.

* * * * *